US00PP27522P2

(12) United States Plant Patent
Lee

(10) Patent No.: US PP27,522 P2
(45) Date of Patent: Jan. 3, 2017

(54) AZALEA PLANT NAMED 'LAZAMORINK'

(50) Latin Name: ***Rhododendron* hybrid**
Varietal Denomination: Lazamorink

(71) Applicant: Robert Edward Lee, Independence, LA (US)

(72) Inventor: Robert Edward Lee, Independence, LA (US)

(73) Assignees: Robert Edward Lee, Independence, LA (US); Plant Development Services, Inc., Loxley, AL (US)

( * ) Notice: Subject to any disclaimer, the term of this patent is extended or adjusted under 35 U.S.C. 154(b) by 0 days.

(21) Appl. No.: 14/756,218

(22) Filed: Aug. 18, 2015

(51) Int. Cl.
*A01H 5/00* (2006.01)

(52) U.S. Cl.
USPC ..... Plt./239

(58) Field of Classification Search
USPC ..... Plt./238, 239, 240
See application file for complete search history.

*Primary Examiner* — Susan McCormick Ewoldt
(74) *Attorney, Agent, or Firm* — Audrey Charles

(57) ABSTRACT

A new and distinct cultivar of Azalea plant named 'Lazamorink', characterized by its semi-double type, deep pink-colored flowers, dark green-colored foliage, moderately vigorous, compact, upright-mounded growth habit and strong multi-seasonal reblooming, is disclosed.

1 Drawing Sheet

Latin name of genus and species of plant claimed: *Rhododendron* hybrid.

Variety denomination: 'Lazamorink'.

BACKGROUND OF THE INVENTION

The present invention relates to a new and distinct cultivar of Azalea plant botanically known as *Rhododendron* hybrid and hereinafter referred to by the cultivar name 'Lazamorink'.

The new cultivar originated in a controlled breeding program in Independence, La. during the spring of 1997. The objective of the breeding program was the development of Azalea cultivars with attractive flower color with multi-seasonal blooming and that perform well in the garden.

The new Azalea cultivar is the result of open-pollination. The female (seed) parent of the new cultivar is Autumn Rouge 'Conlea', U.S. Plant Pat. No. 10,438, characterized by its semi-double type, dark pink-colored flowers, dark green-colored foliage, and vigorous, semi-upright growth habit. The male (pollen) parent of the new cultivar is unknown however the female was outdoors and in close proximity to numerous proprietary hybrids that had cold hardiness, compact growth habit, and multi-seasonal blooming traits. The new cultivar was discovered and selected as a single flowering plant within the progeny of the above stated open-pollination during the fall of 2002 in a controlled environment in Independence, La.

Asexual reproduction of the new cultivar by terminal stem cuttings since the fall of 2002 in Independence, La. and later in Loxley, Ala. and Irvington, Ala. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Lazamorink' as a new and distinct cultivar of Azalea plant:

1. Semi-double type, deep pink-colored flowers;
2. Dark green-colored foliage;
3. Moderately vigorous, compact, upright-mounded growth habit; and
4. Strong multi-seasonal reblooming.

Plants of the new cultivar differ from plants of the female parent primarily in having a lighter flower color, reduced growth vigor, and a different growth habit.

Of the many commercially available Azalea cultivars, the most similar in comparison to the new cultivar is Autumn Empress 'Conles', U.S. Plant Pat. No. 12,109. However, in side by side comparisons, plants of the new cultivar differ from plants of 'Conles' in at least the following characteristics:

1. Plants of the new cultivar have a lighter pink flower color than plants of 'Conles';
2. Plants of the new cultivar are more compact than plants of 'Conles'; and
3. Plants of the new cultivar have a leaf color different from plants of 'Conles'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Lazamorink'. The plants were grown in 2-gallon containers for 9 months outdoors in Irvington, Ala. Plants were given one pinch at transplant.

DETAILED BOTANICAL DESCRIPTION

Figure 1:
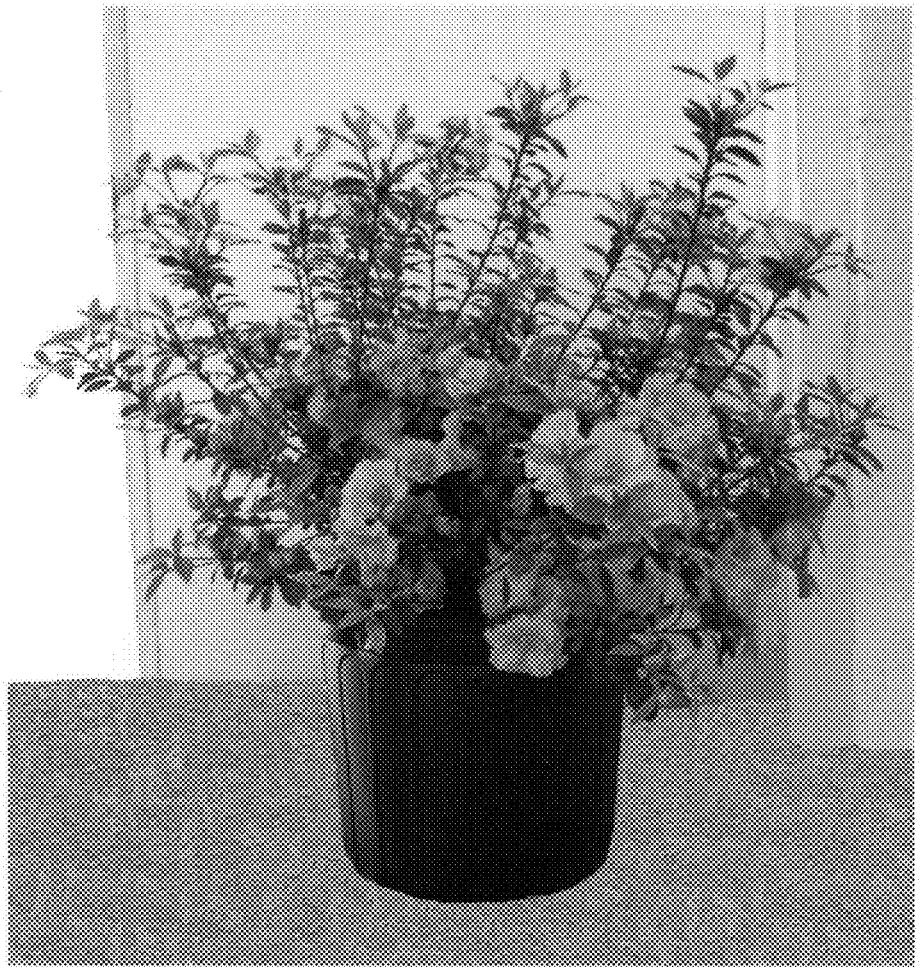
FIG. 1 illustrates a side view of the overall growth and flowering habit of 'Lazamorink'.
Figure 2:
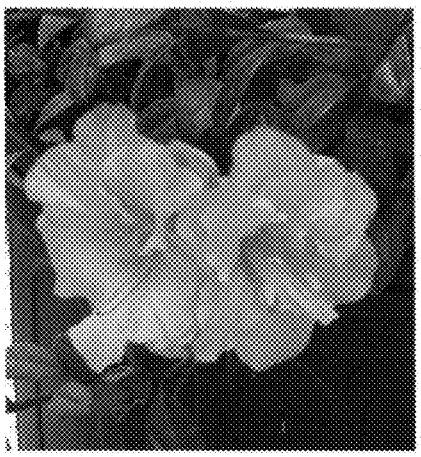
FIG. 2 illustrates a close-up view of an individual flower of 'Lazamorink'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in April 2015 under natural light conditions in West Chicago, Ill.

The following descriptions and measurements describe plants produced from semi-hardwood stem cuttings from stock plants. Rooted plants, liners, were transplanted into 2-gallon containers utilizing a soilless growth medium. Plants were given one pinch at transplant and grown for approximately 9 months outside in Irvington, Ala. under conditions comparable to those used in commercial practice. Average winter temperatures ranged from 63° F. to 42° F. (17° C. to 5° C.) and average summer temperatures ranged from 91° F. to 72° F. (33° C. to 22° C.). Measurements and numerical values represent averages of typical plants.

Botanical classification: *Rhododendron* hybrid cultivar Lazamorink.

Parentage:

*Female parent*.—Autumn Rouge 'Conlea', U.S. Plant Pat. No. 10,438.

*Male parent*.—Unknown.

Propagation:

*Type cutting*.—Semi-hardwood stem cuttings.

*Time to initiate roots, summer*.—Approximately 25 to 30 days.

*Time to produce a rooted cutting, summer*.—Approximately 60 to 70 days.

*Root description*.—Fine, fibrous; initially white in color becoming light brown with age.

*Rooting habit*.—Freely branching, dense.

Plant description:

*Commercial crop time*.—Approximately 10 months from a rooted cutting to finish in a 1-gallon container.

*Growth habit and general appearance*.—Perennial, evergreen flowering subshrub; moderately vigorous, upright-mounded growth habit.

*Size*.—Height from soil level: Approximately 48.0 cm. Width: Approximately 68.0 cm.

*Branching habit*.—Two to three main trunks, freely branching, pinching improves lateral branching. Quantity of primary lateral branches per plant: Approximately 7. Quantity of secondary lateral branches: Approximately 3 to 9 per primary branch.

*Primary lateral branches*.—Strength: Very strong, rigid. Length: Approximately 22.5 cm. Diameter at midpoint: Approximately 7.0 mm. Texture: Woody, rough. Color: 200A to 200B.

*Secondary lateral branches*.—Strength: Very strong, flexible. Length: Approximately 26.5 cm. Diameter at midpoint: Approximately 3.0 mm. Length of central internode: Approximately 1.4 cm. Texture: Densely pubescent, hairs appressed. Color of young branches: 187B to 187C. Color of mature branches: N199B to N199C.

Foliage description:

*General description*.—Leaf retention: Very good winter leaf retention. Fragrance: None detected. Form: Simple. Arrangement on flowering stem: Alternate.

*Leaves*.—Aspect: Acute angle to stem, blades extend downward with age. Shape: Elliptic. Margin: Entire. Apex: Acute, mucronulate. Base: Broadly attenuate. Venation pattern: Pinnate, finely reticulate. Length of mature leaf: Approximately 3.0 cm. Width of mature leaf: Approximately 1.5 cm. Texture of upper and lower surfaces: Densely pubescent, hairs appressed, leathery. Color of upper surface of young foliage: 137B with venation of 146D or indistinguishable from leaf surface. Color of lower surface of young foliage: Closest to 138B with venation of 146D or indistinguishable from leaf surface. Color of upper surface of mature foliage: N137A tinted with 187A and with venation of 146D or indistinguishable from leaf surface. Color of lower surface of mature foliage: Closest to 146B faintly tinted with 187A and with venation of 146D or indistinguishable from leaf surface.

*Petiole*.—Length: Approximately 5.0 mm. Width: Approximately 2.0 mm. Texture: Densely pubescent, hairs appressed. Color: 146C tinted with 187A.

Flowering description:

*Flowering habit*.—'Lazamorink' flowers in spring from early March to mid-April and then remontant flowering during spring and autumn.

*Lastingness of individual flower on the plant*.—Flowers are durable and long-lasting; depending on the temperature flowers can last approximately one week on the plant.

Flower description:

*General description*.—Type: Semi-double, non-persistent. Arrangement: Terminal clusters of 3 to 5 flowers and buds in whorls, approximately 50 clusters per plant. Fragrance: None detected.

*Bud*.—Rate of opening: Generally takes 2 to 3 days for bud to progress from first color to fully open flower.

*Bud just before opening*.—Shape: Ovoid. Length: Approximately 2.3 cm. Diameter: Approximately 1.3 cm. Texture: Glabrous. Color: N57D.

*Corolla*.—Diameter: Approximately 6.0 cm. Depth: Approximately 4.0 cm.

*Petals*.—Quantity: Outer whorl of 5 petals, fused to form a shallow tube that extends 1.7 cm from the base to the free portions between the upper and lateral petals and extends 1.0 cm to 5.0 mm from the base to the free portions of the lower petals, unfused portions imbricate; inner whorl of 6 to 9 staminate petaloids. Shape: Obovate with approximately 1 to 2 of the petaloids being irregularly shaped. Appearance: Velvety. Margin: Entire, undulate. Apex: Obtuse. Length of free portion of petals: Approximately 2.3 cm. Width of petals: Approximately 2.7 cm to 2.9 cm. Length of petaloids: Approximately 3.3 to 3.5 cm. Width of obovate-shaped petaloids: Approximately 2.2 cm to 2.5 cm. Texture of upper surface: Glabrous, tube portion densely pubescent with very short hairs. Texture of lower surface: Glabrous. Color of upper surface when first and fully open: N57D to lighter than N57D with speckles of 60B on upper and lateral petals and petaloids. Color of lower surface when first and fully open: Lighter than N57D with central streaks of NN155D on outer whorl.

*Sepals*.—Quantity per flower: 5, fused at base. Shape: Ovate. Apex: Acute. Margin: Erose. Length: Approximately 8.0 mm. Width: Approximately 4.0 mm. Texture of upper (inner) surface: Glabrous.

Texture of lower (outer) surface: Densely pubescent, hairs appressed. Color of upper (inner) surface: 144A. Color of lower (outer) surface: 144B.

*Peduncle*.—Strength: Strong, flexible. Aspect: Acute angle to stem. Length: Approximately 1.1 cm. Diameter: Approximately 2.0 mm. Texture: Densely pubescent, hairs appressed. Color: 145B to 145C heavily tinted with 185A.

*Reproductive organs*.—Androecium: Stamen quantity: Approximately 1 to 4, petaloid. Stamen length: Approximately 2.5 to 3.5 cm with 1 to 2 irregularly shaped petaloids attached to base and up to 2.3 cm in length. Filament length: Approximately 2.4 to 3.4 cm. Filament texture: Lower portion densely pubescent with very short colorless glands. Filament color: N57C. Anther shape: Bilobed, dorsifixed. Anther length: Approximately 2.0 mm. Anther color: N79C darkens to 186B with age. Pollen amount: Moderate. Pollen color: NN155A. Gynoecium: Pistil quantity: 1 per flower, often malformed. Pistil length: Approximately 4.2 cm. Stigma shape: Round, capitate, often split if pistil malformed. Stigma length: Approximately 1.0 mm. Stigma color: 145A. Style length: Approximately 3.7 cm. Style color: 60B. Ovary length: Approximately 4.0 mm. Ovary texture: Densely pubescent with long white hairs. Ovary color: 144A.

Seed and fruit production: Neither seed nor fruit production has been observed.

Garden performance and temperature tolerance: Plants of the new Azalea have been observed to be very tolerant to rain, wind and are suitable for USDA Hardiness Zones 7 to 9.

Disease and pest resistance: Resistance to pathogens and pests common to Azalea has not been observed.

What is claimed is:

1. A new and distinct cultivar of Azalea plant named 'Lazamorink', substantially as herein illustrated and described.

* * * * *